United States Patent
Gramnäs

(12) 
(10) Patent No.: US 6,402,789 B1
(45) Date of Patent: Jun. 11, 2002

(54) LOCKING DEVICE INTENDED AS A FASTENING MEANS FOR A PROSTHESIS

(76) Inventor: Finn Gramnäs, Hästskovägen 5, 511 56 Kinna (SE)

( * ) Notice: Subject to any disclaimer, the term of this patent is extended or adjusted under 35 U.S.C. 154(b) by 0 days.

(21) Appl. No.: 09/555,195

(22) PCT Filed: Nov. 27, 1998

(86) PCT No.: PCT/SE98/02170
§ 371 (c)(1),
(2), (4) Date: May 25, 2000

(87) PCT Pub. No.: WO99/32056
PCT Pub. Date: Jul. 1, 1999

(30) Foreign Application Priority Data

Nov. 27, 1997 (SE) ................................................ 9704364

(51) Int. Cl.$^7$ ................................................. A61F 2/80
(52) U.S. Cl. ............................ 623/38; 623/83; 403/325
(58) Field of Search ...................... 623/33–38; 403/131, 403/129, 325, 330, 350

(56) References Cited

U.S. PATENT DOCUMENTS

| | | | | |
|---|---|---|---|---|
| 3,693,484 A | * | 9/1972 | Sanderson, Jr. | 403/325 |
| 3,947,897 A | | 4/1976 | Owens | 3/2 |
| 4,906,123 A | * | 3/1990 | Weskamp et al. | 403/322 |
| 5,141,355 A | * | 8/1992 | Stillwagon | 403/325 |
| 5,547,308 A | * | 8/1996 | Wright | 403/325 |
| 6,065,897 A | * | 5/2000 | Lutz, III | 403/325 |
| 6,106,559 A | * | 8/2000 | Meyer | 623/33 |
| 6,139,586 A | * | 10/2000 | Wagner | 623/44 |
| 6,152,645 A | * | 11/2000 | Sanford | 403/328 |

FOREIGN PATENT DOCUMENTS

| | | | | |
|---|---|---|---|---|
| GB | 772203 | 4/1957 | | 44/3 B |
| WO | WO 94/04101 | 8/1993 | | A61F/2/50 |
| WO | WO 94/04102 | 8/1993 | | A61F/2/62 |

\* cited by examiner

Primary Examiner—Bruce Snow
(74) Attorney, Agent, or Firm—Gardner Carton & Douglas

(57) ABSTRACT

A locking device for securing a prosthesis to a cylindrical part attached to a wearer. The device allows insertion of the cylindrical part, such as a pin, to be inserted into the locking mechanism at an oblique angle.

14 Claims, 5 Drawing Sheets

//LOCKING DEVICE INTENDED AS A
FASTENING MEANS FOR A PROSTHESIS

BACKGROUND OF THE INVENTION

The present invention refers to a locking device intended as a fastening means for prostheses, such as leg- and arm prostheses, of the kind where the prosthesis is to be fastened to a cylindrical part such as a pin, an axle, a tube or the like. It can for example be used in such cases where a silicone stocking is applied on the leg- or arm stump, said stocking having a plastic cup moulded into the bottom thereof and said cup having a pin attached thereto. The leg- and arm stump provided with a silicone stocking is passed into a prosthesis sleeve connected to the prosthesis, said prosthesis sleeve is provided with a locking device for the pin.

In the international patent application WO 94/04101 it is shown a fastening means intended for a prosthesis, said fastening means comprises a tilted washer, which by spring force is kept in tilted position and by this is locked to the pin. The degree of tilting of the washer can be reduced by means of an actuating means by which the locking to the pin can be released.

In DE-C-1,097,217 there is shown a clamping device for axles and tubes and which comprises a ring of balls arranged in a cage, which by means of spring action is pressed into a conical seat, at which the locking device is locked to the axle in axial direction, said clamping device further comprises actuating means for releasing the ring of balls from the conical seat. The actuating means comprises a fork-shaped member which grips the pin and which is provided with inclined surfaces cooperating with inclined surfaces on a holding-on ring, so that the holder-on ring and the ring of balls by wedge action is displaced along the pin. There is no indication that this clamping device would be intended to be used in connection with prostheses. Besides it is designed so that the axle only may be passed into the locking device in a completely straight position.

OBJECT AND MOST IMPORTANT FEATURES OF THE INVENTION

The object of the present invention is to provide a locking device of the kind mentioned above, which should be positionable in a stepless way, it should permit rotation around the pin also in locked position, it should be relatively insensitive to dirt and threads from textiles which easily may penetrate into it, it should permit the pin to be easily inserted into it also in a slightly oblique position and it should lock from movement out of the locking mechanism in a stepless way.

The locking device according to the invention is characterized by the fact that it comprises a cage with a ring of balls arranged therein, said ring of balls by means of spring action is pressed into a conical seat in the cage, at which the locking device is locked to the pin or the like in axial direction while rotational movement is admitted, said locking device further comprises actuating means for releasing the ring of balls from the conical seat, at which the cage is arranged in a housing provided with a through opening for receiving said pin or the like, said opening has a larger diameter than the pin or the like in order to admit this to be inserted also in an oblique position.

DESCRIPTION OF THE DRAWINGS

The invention will in the following be closer described with reference to some embodiments shown in the accompanying drawings.

DESCRIPTION OF EMBODIMENTS

Figure 1:
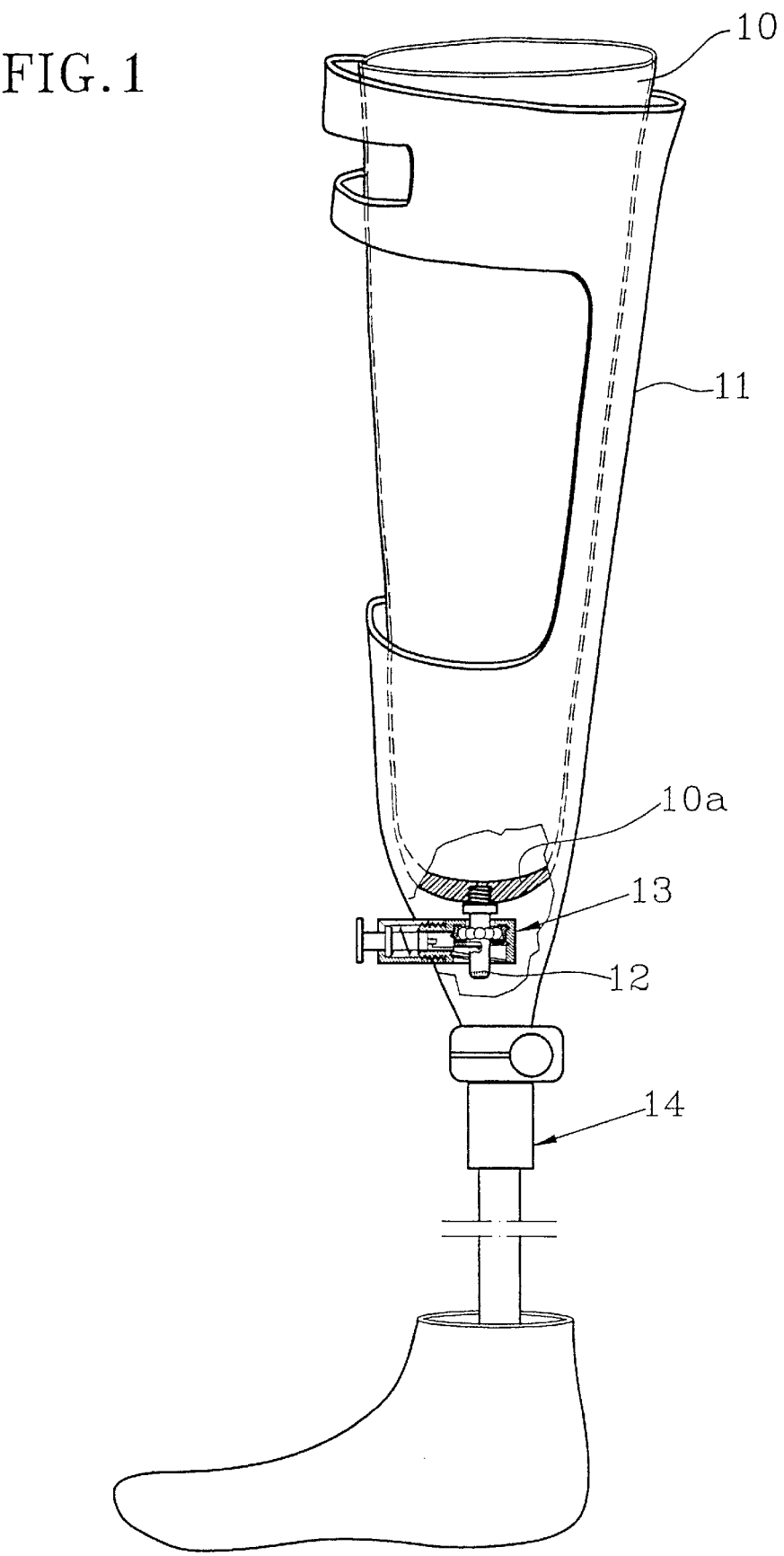
FIG. 1 shows a leg prosthesis provided with a locking device according to the invention.
Figure 2:
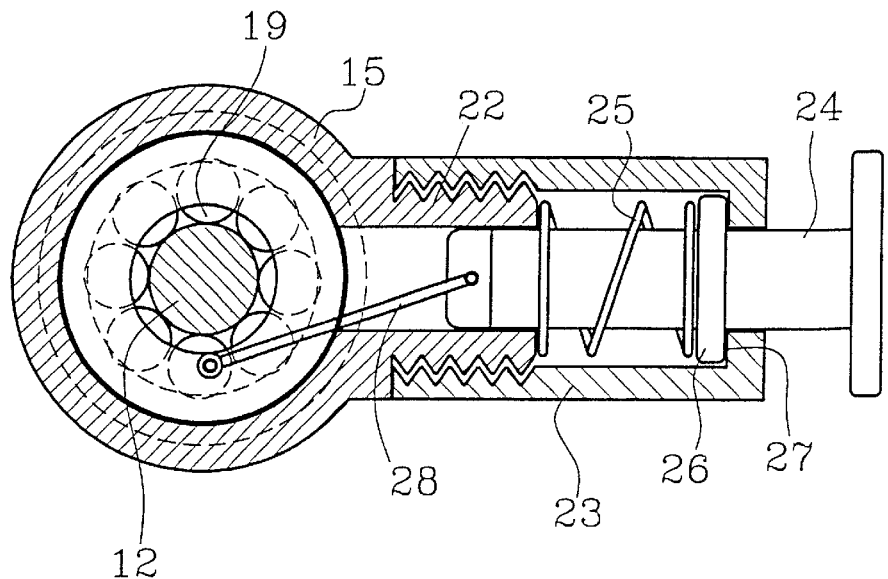
FIG. 2 is a horizontal longitudinal section through an embodiment of the locking device.

In FIG. 1 there is shown a silicone stocking 10 intended to be passed on an amputated leg. A plastic cup 10a is moulded into the bottom of the silicone stocking 10 and said plastic cup having a cylindrical pin 12 threaded into it. The amputated leg stump which is provided with the silicone stocking 11 is passed into a prosthesis sleeve 11. The prosthesis sleeve has a locking device 13 for the pin 12 and is connected to a prosthesis, in the shown example a leg prosthesis 14.

Figure 3:
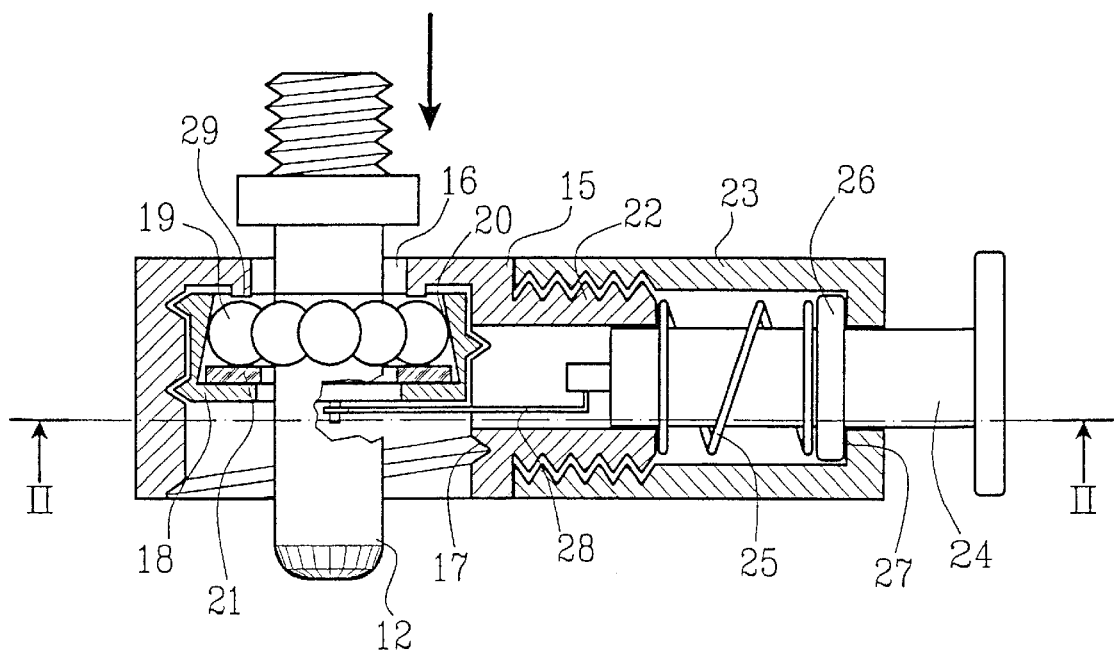
FIG. 3 is a vertical longitudinal section through the locking device in connecting position.
Figure 4:
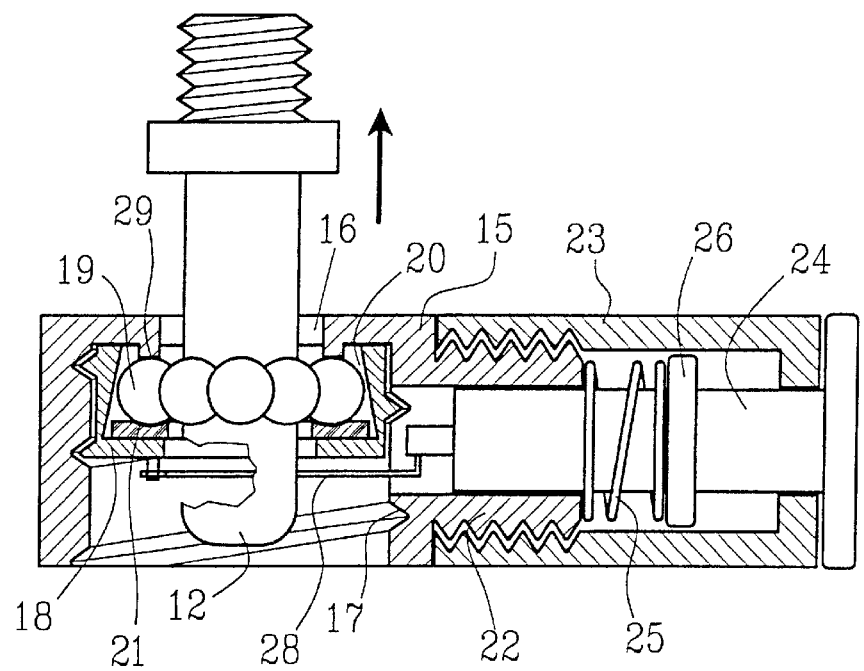
FIG. 4 is a corresponding section as in FIG. 3 but in disconnecting position.
Figure 5:
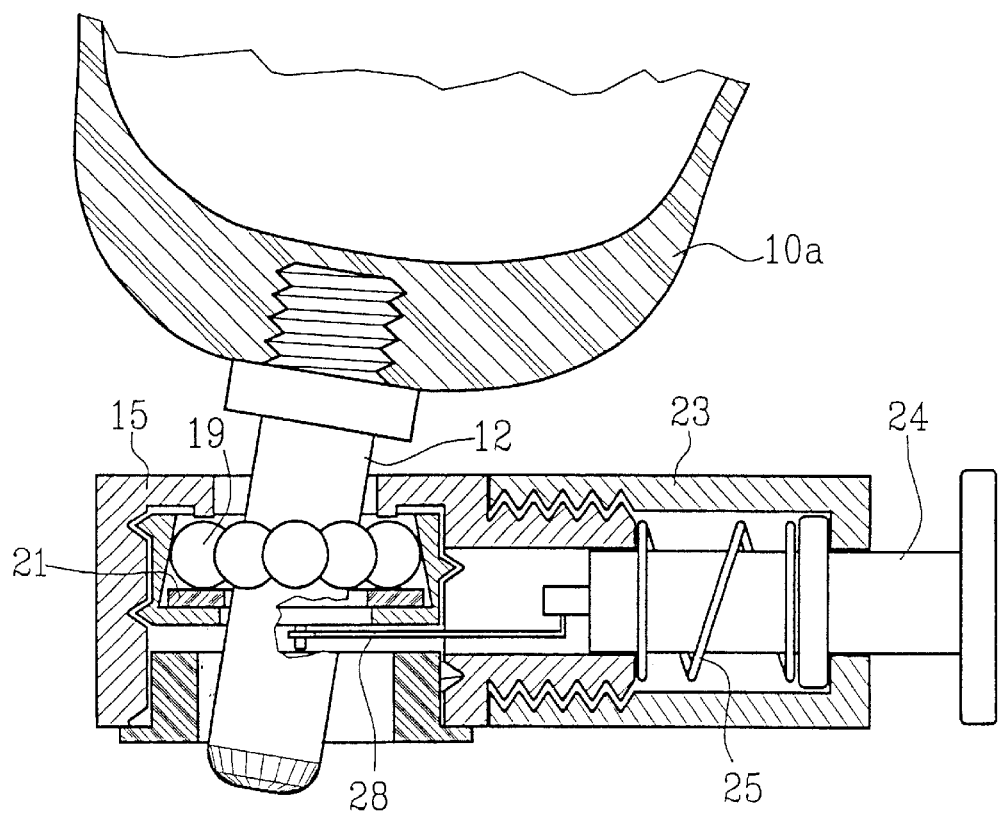
FIG. 5 is a corresponding section as in FIG. 3 showing the pin with a prosthesis sleeve connected thereto and inserted into the locking device in an oblique position.

The locking device, which is shown more in detail in FIGS. 2–5, comprises a housing 15 with a through opening 16 for receiving the pin 12. The opening 16 has a larger diameter than the pin 12, at which this may be inserted into the opening also in a slightly oblique position, which is shown in FIG. 5.

The opening 16 is provided with a widened threaded portion 17, in which a cage 18 for a ring of balls 19 is threaded. The cage 18 is provided with a conical seat 20 for the ring of balls 19 with the more narrow portion directed towards the prosthesis sleeve 11. A resilient washer 21, e g a rubber washer, presses initially the ring of balls 19 into the conical seat 20, at which the ring of balls is locked around the pin 12. The locking effect is accomplished by wedging action between the balls and the pin. The pin 12 can with a low resistance be passed through the ring of balls 19 also in a slightly oblique position and be positioned in a stepless manner and locked in the locking device. The locking device locks immediately and without play and anywhere along the pin if one tries to withdraw it from the ring of balls. This type of locking by means of a ring of balls pressed into a conical seat is relatively insensitive to dirt and threads from textiles which easily may penetrate through the opening 16.

The locking device is shown in locking position in FIG. 3 and 5. In this position the locking device is thus locked to the pin 12 in axial direction while rotational movements between the pin and the locking device are admitted. The pin 12 is locked by wedging action automatically when one tries to withdraw it, while it may freely be inserted into and positioned in an optional position in the locking device.

The amputated leg stump is often swollen in the morning and can therefore not be passed completely down into the prosthesis sleeve 11 but will sink down gradually during the day. The locking device according to the invention often admits this since locking is accomplished completely without play. With this is meant that every minimal movement of the pin downwards in the locking device will be taken up thereby and the locking device will lock immediately if the pin moves in opposite direction, the locking direction. This play-free locking function has the further advantage that irritating click-sounds are avoided, which otherwise occur if there is a play in the locking mechanism.

The housing 15 is provided with a radially towards the opening 16 directed tubular connection piece 22 provided with external threads and on which a holder- and guide member 23 for a push rod 24 is threaded. The tubular connection piece 22 also forms a part of the guide for the push rod 24. The push rod is springloaded by means of a spring 25 which is fixed between a collar 26 on the push rod and a support surface on the connection piece 22. The push rod 24 is by the spring 25 kept in the extended position shown in FIG. 2, and 5, where the collar 25 is in contact with a support surface 27 on the holder- and guide member 23.

A lever arm 28 is attached to the push rod 24 and the holder 18 in such a way that displacement of the push rod 24 in axial direction provides a rotation of the holder 18 in the housing 15. When thus the push rod 24 against the action of the spring 25 pushes the push rod 24 inwards to the position shown in FIG. 4 the holder 18 is rotated upwards according to the drawing. The ring of balls 19 will then also be displaced upwards but meets a shoulder 29 in the housing 15 which prevents further displacement upwards of the ring of balls 19. The holder 18 can however move further a small distance upwards to such an extent that the ring of balls 19 leaves the conical seat 20, at which the locking to the pin 12 is disconnected. The prosthesis 14 can in this position be removed from the pin 12.

The spring 25 besides contributes in locking position to actively draw the holder 18 downwards according to FIG. 3, at which the balls 19 are kept away from the shoulder 29 so that they are kept in the conical seat 20 and the locking around the pin is secured.

It should be noted that it would be possible also at strong jerks or pulling forces to accomplish rotation of the holder 18 out of locking position according to FIG. 3 to a released position according to FIG. 4 at which the prosthesis can be removed from the pin 12. This is obtained by the relatively large pitch of threads of the holder and the housing. In normal use however the locking of the ring of balls to the pin should be secured. The force required to jerk the pin loose from the locking device can be adjusted by choosing the spring force of the spring 25.

As mentioned above and which is also shown in FIG. 5 the pin 12 can be inserted into and positioned in a slightly oblique position in the locking device. The fact that the pin without problems can be inserted into, locked and released in an oblique position is a very big advantage. It is common that the soft silicone stocking 10 ends up somewhat askew when putting it on the leg stump. The pin 12 will then not end up in the centre of the stump end. Even if one manages to insert the pin 12 into the hole of a conventional locking mechanism in an oblique position, the tilting forces that remains when the pin is forced to an upright position can be so large that the pin 12 seizes in the locking device. This can in turn involve that it becomes difficult or even impossible to take the prosthesis off from the leg stump.

The obliqueness shown in the drawing is about 10°. Depending on the design of the conical seat 20 a larger angular adjustment of the pin may be permitted. The balls 19 will adjust themselves in order to adapt to the oblique pin 12.

Figure 6:
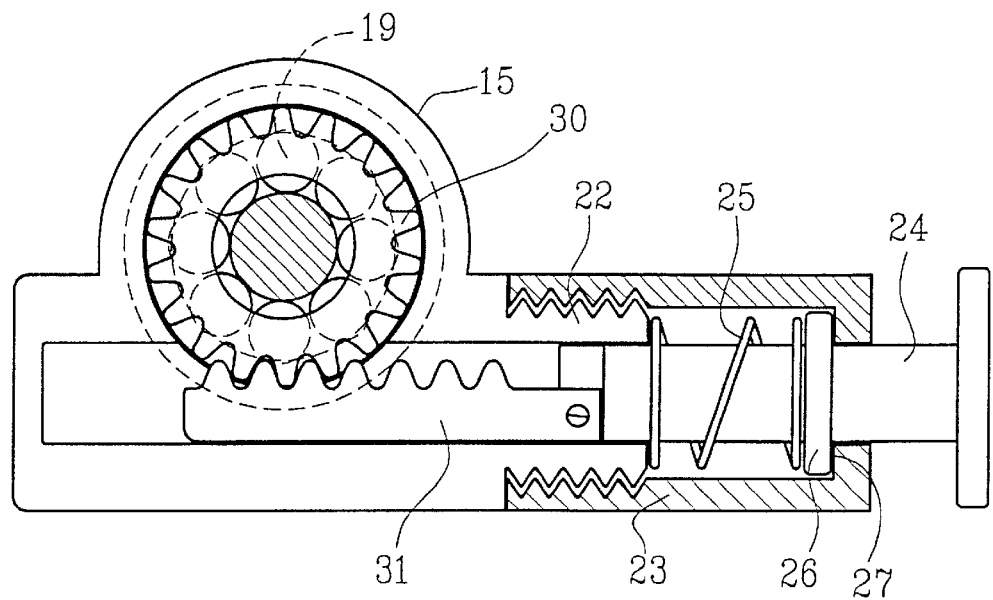
FIG. 6 is a horizontal longitudinal section through a modified embodiment of the locking device.
Figure 7:
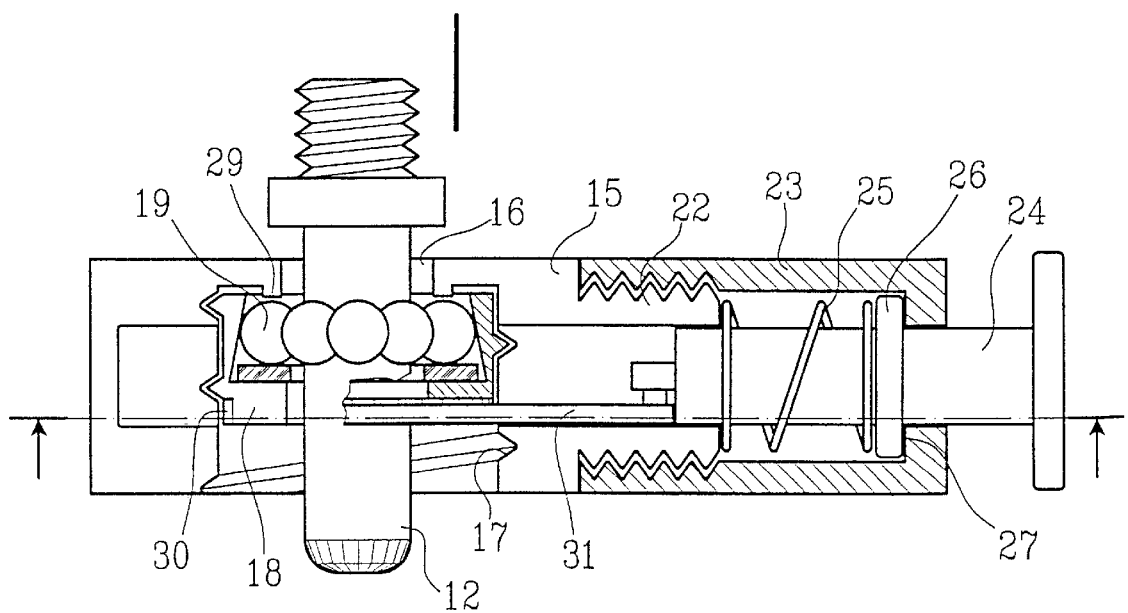
FIG. 7 is a vertical longitudinal section through the locking device according to FIG. 6.

In FIG. 6 and 7 is shown a modified embodiment of the locking device according to which the holder 18 is provided with an external gear ring 30 intended to cooperate with a gear rack 31 connected to the push rod 24. By pressing the push rod 24 inwards the gear rack 31 will provide a rotation of the holder 18 in the housing 15.

Figure 8:
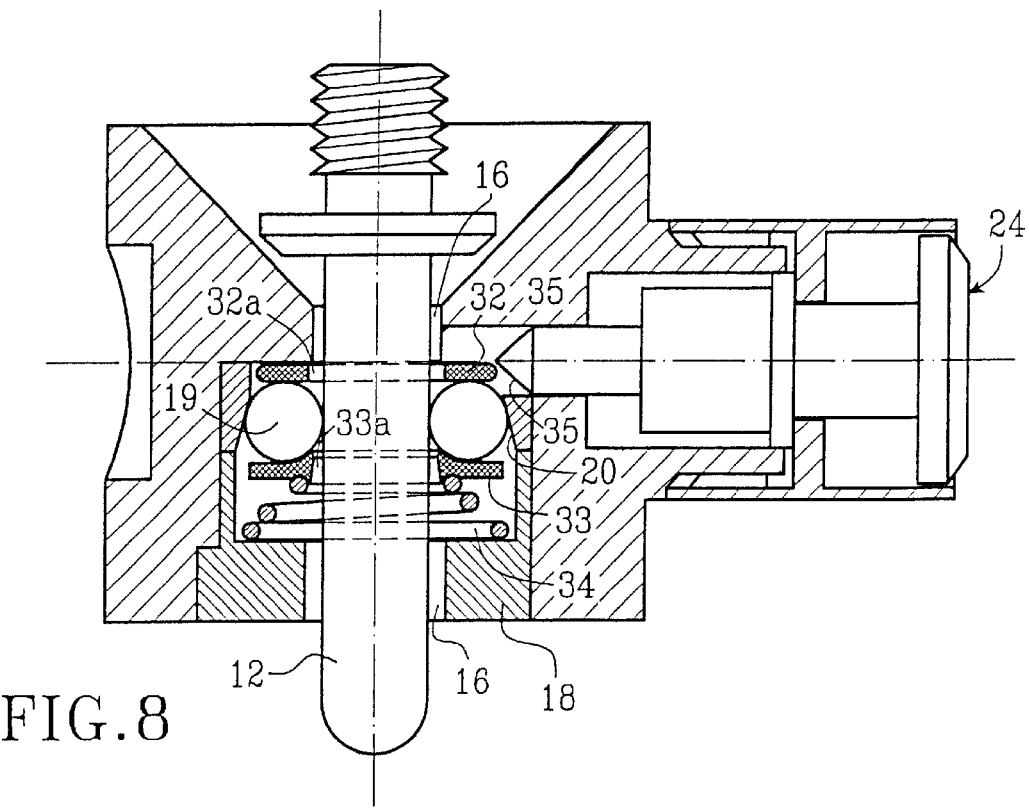
FIG. 8 is a vertical longitudinal section through a further embodiment of the invention.
Figure 9:
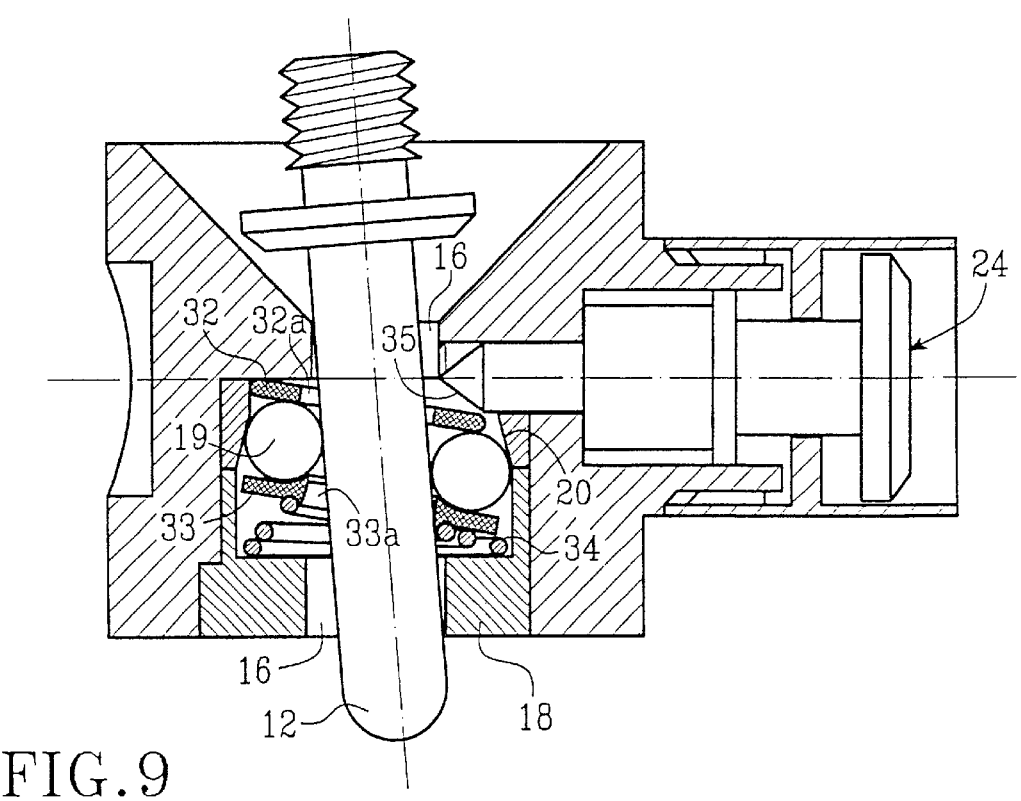
FIG. 9 shows the embodiment according to FIG. 8 in disconnecting position.

In FIGS. 8 and 9 there is shown a further embodiment according to which the ring of balls 19 is arranged between two washers, a first washer 32 and a second washer 33. The ring of balls 19 will be pressed into the conical seat 20 of the holder 29 by means of a compression spring 34 arranged between the holder 18 and the second washer 33. The second washer 33 is preferably of a resilient material, so that the pressure from the spring 34 is distributed individually on each ball. The two washers 32 and 33 both have through openings 32a and 33a respectively, which have a larger diameter than the diameter of the pin 12, in order to permit this to be inserted obliquely.

The actuating means for releasing the ring of balls 19 from the conical seat 20 is also in this case a push rod 24. This is at its end provided with an inclined surface 35 intended to cooperate with the first washer 32 for pressing down the edge thereof against the action of a compression spring 34, at which the ring of balls 19 is tilted and on one side leaves its engagement with the conical seat 20 of the holder 18. The locking to the pin 12 by that ceases.

It is of course possible to modify the actuating means 24, 35 so that this acts by pressing down the whole first washer 32 and not only one side thereof.

The invention is of course not limited to the embodiments shown in the drawings and described above but can be modified within the scope of the claims.

What is claimed is:

1. A locking device intended as a fastening means for prostheses, the prosthesis is fastened to a cylindrical part, the locking device comprising:
   a cage comprising:
      a ring of balls;
      a conical seat positioned adjacent to the cylindrical part; and
      means for spring action;
      wherein said ring of balls is pressed into the conical seat in the cage by the spring action means in an axial direction while rotational movement is admitted;
   means for actuating, the actuating means adapted for releasing the ring of balls from the conical seat; and
   a housing provided with a through opening for receiving said cylindrical part;
      wherein said opening has a larger diameter than the pin and is sized such that the pin may enter the housing and remain locked therein at an oblique angle with respect to the housing.

2. The locking device according to claim 1, wherein the spring action means comprises a resilient element.

3. The locking device according to claim 2, wherein a first washer is disposed on the ring of balls opposite the resilient element, the first washer being actuatable by said actuating member for pressing the ball of rings out of engagement with the conical seat of the cage against the action of the resilient element.

4. The locking the device according to claim 3, wherein the resilient element comprises a second washer and a compression spring fixed between the second washer and the cage.

5. The locking device according to claim 4, wherein the actuating means comprises a manually actuatable push rod which cooperates with the first washer by means of an inclined surface for pressing the first washer and by that also the ring of balls and the second washer downwards against the action of the compression spring, at which the ring of balls is brought out of engagement with the conical seat of the cage.

6. The locking device according to claim 5, wherein the first and second washer are provided with openings for the pin, said openings having a larger diameter than the pin and the push rod with its included surface acts only on one side of the first washer, at which a tilting of the first and the second washer and of the ring of balls is provided so that the pin is released.

7. The locking device according to claim 1, wherein the cage is provided with a threaded outside and is adapted to be threaded into the housing, and wherein said actuating means provides a rotation of the cage in the housing such that the ring of balls is released from the conical seat of the holder.

8. The locking device according to claim 7, wherein the actuating means comprises a manually actuatable push rod arranged substantially radially to the opening in the housing.

9. The locking device according to claim 8, wherein the push rod is axially displaceable in a means for holding and guiding connected to the housing, the holding and guiding means extending substantially to the opening of the housing.

10. The locking device according to claim 8, wherein the actuating means further comprises a lever arm, the lever arm having a first end and a second end, the first end connected to the push rod and the second end connected to the cage.

11. The locking device according to claim 8, wherein the actuating means further comprises a gear rack having a first end and second end, the first end connected to the push rod and the second end adapted to cooperate with an outer gear ring arranged on the cage.

12. The locking devices according to claim 8, wherein the push rod is spring-loaded and against the action of said spring can be brought to a position in which it provides a rotation of the cage in the housing so that the ring of balls is released from the conical seat of the cage.

13. The locking device according to claim 12, wherein the housing is provided with a shoulder arranged to limit the axial movement of the ring of balls in connection with rotating the cage to a releasing position, such that the ring of balls is pushed out from the conical seat at continued rotation of the cage.

14. The locking device according to claim 13, wherein the cage is adapted to releasably rotate.

* * * * *